(12) United States Patent
Blandino et al.

(10) Patent No.: US 8,445,051 B2
(45) Date of Patent: May 21, 2013

(54) THIOL-CONTAINING FRAGRANCE AND FLAVOR MATERIALS

(75) Inventors: Maureen Blandino, North Bergen, NJ (US); Henry Van Den Heuvel, River Vale, NJ (US); Michael E. Lankin, High Bridge, NJ (US)

(73) Assignee: Takasago International Corporation, Tokyo (JP)

( * ) Notice: Subject to any disclaimer, the term of this patent is extended or adjusted under 35 U.S.C. 154(b) by 0 days.

(21) Appl. No.: 13/070,284

(22) Filed: Mar. 23, 2011

(65) Prior Publication Data

US 2011/0256071 A1 Oct. 20, 2011

Related U.S. Application Data

(63) Continuation of application No. PCT/US2009/060469, filed on Oct. 13, 2009.

(60) Provisional application No. 61/104,389, filed on Oct. 18, 2008.

(51) Int. Cl.
*A23L 1/22* (2006.01)
*A61Q 13/00* (2006.01)

(52) U.S. Cl.
USPC ............ 426/535; 560/125; 426/534; 426/650

(58) Field of Classification Search
None
See application file for complete search history.

(56) References Cited

U.S. PATENT DOCUMENTS

| | | | |
|---|---|---|---|
| 4,318,934 A | 3/1982 | Boden | |
| 6,878,366 B2 * | 4/2005 | Dewis et al. | 424/65 |
| 7,105,194 B2 * | 9/2006 | Gassenmeier et al. | 426/535 |
| 2008/0200359 A1 | 8/2008 | Smets et al. | |

OTHER PUBLICATIONS

W.J. Waddell, S.M. Cohen, V.J. Feron, J.I. Goodman, L.J. Marnett, P.S. Portoghese, I.M.C.M. Ri etjens, R.L. Smi th, T.B. Adams ,C. Lucas Gavin, M.M. McGowen, and M.C. Williams. GRAS Flavoring Substances 23: The 23rd publication by the FEMA Expert Panel, Food Technology, Aug. 2007, pp. 22-24, 26-28, and 30-49.*
CAS Registry for Registry No. 888021-82-7.*
Spanish language version of Susancias Permitidas como Aditivos en Alimentos dated Jul. 17, 2006—provided by United Mexican States.*
English translation of Spanish language version of Susancias Permitidas como Aditivos en Alimentos dated Jul. 17, 2006—provided by United Mexican States.*
CAS Registry for Registry No. 888021-82-7. (2012).*
International Search REport and Written Opinion for PCT/US2009/060469, dated Dec. 10, 2009.

* cited by examiner

*Primary Examiner* — Brian Gulledge
*Assistant Examiner* — Michael P Cohen
(74) *Attorney, Agent, or Firm* — Baker Botts LLP

(57) ABSTRACT

One aspect of the present invention provides a compound represented by formula (I),

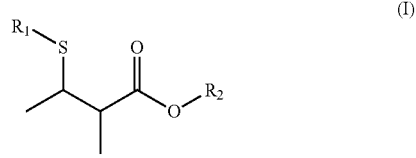

wherein, $R_1$ is hydrogen or an acetyl group and $R_2$ is a $C_{1-3}$ straight chain or branched alkyl group. Another aspect of the present invention provides flavor or fragrance compositions comprising at least one compound of formula (I).

12 Claims, No Drawings

THIOL-CONTAINING FRAGRANCE AND FLAVOR MATERIALS

CROSS REFERENCE TO RELATED APPLICATIONS

This application is a continuation of International Application No. PCT/US2009/060469, filed Oct. 13, 2009, which claims priority to U.S. Provisional Application Ser. No. 61/104,389, filed Oct. 18, 2008, both of which are hereby incorporated by reference in their entireties, and from which priority is claimed.

FIELD OF THE INVENTION

The present application relates to thiol-containing compounds for use in fragrance and flavor compositions.

BACKGROUND OF THE INVENTION

There is a continuing interest in the preparation of synthetic fragrance and flavor components and their use in consumer products. Thiols, which are traditionally associated with strong unpleasant odors, can, in certain cases, also be used to impart fruity notes in both flavor and fragrance compositions.

Specific thiol materials for use in flavor and/or fragrance have been disclosed. U.S. Pat. No. 6,878,366, discloses ethyl 3-mercaptobutyrate as a flavor and fragrance material. The compound is prepared from ethyl crotonate and sodium hydrogen sulfide to make the disulfide dimer, which is then reduced to the free thiol.

U.S. Pat. No. 5,565,473 describes the synthesis of ethyl 3-mercapto-2-methylpropanoate and ethyl 3-acetylthio-2-methylpropanoate by thiolacetic acid addition to 2-methyl-2-propenoates. Nielsen and Madsen, Tetrahedron Asym. 1994, 403-410 describe thiolacetic acid addition to ethyl crotonate, followed by deprotection to the free thiol; also for thiolacetic acid addition to methyl crotonate see Hutchinson et al., J. Med. Chem. 1994, 1153-1164. Additions to various methyl butenoates by protected thiols are described in Miyata et al. JOC 1991, 6556-6564; Miyata et al. J. Chem. Soc. Perkins Trans. I. 1993, 2861-2862; Nishimura et al. JOC 2002, 431-434 (phenylthio additions) and Lee et al. Synth. Commun. 1996, 2189-2196 (hexylthio addition to methyl 2-methylbutenoate).

U.S. Pat. No. 7,105,194 discloses 3-mercapto ethyl esters of hexanoates. U.S. Pat. No. 6,899,911 discloses ethyl 4-(thioacetoxy)butyrate as a flavor material. U.S. Published Application No. 2009/232747 claims various ethyl 2-sulfanyl-2-methylpropanoates for use as flavor and/or fragrance materials. U.S. Pat. No. 6,610,346 describes benzyl mercaptan addition to methyl tiglate to yield methyl 3-benzylmercapto-2-methylbutanoate as an intermediate in the synthesis of fragrance materials. JP03074351 describes the preparation of methyl 2-methyl-3-phenysulfinylbutanoate.

International Published Application No. WO 2005/082346 discloses methyl 3-acetylthio-2-methylbutanoate, which is described as a drug intermediate. The free thiol of the free acid, 3-mercapto-2-methylbutanoic acid (chiral) is also described therein as a synthetic intermediate. U.S. Pat. No. 7,071,175 discloses 3-mercapto-substituted carboxylic acids in drug synthesis.

There remains a need and demand for unique fragrance and flavor compositions. There is also a need for more efficient synthesis techniques to prepare components, particularly thiol-containing compounds, for fragrance and flavor compositions.

SUMMARY OF THE INVENTION

It has been found that the thiol addition to alkyl tiglates (e.g., ethyl tiglate) produces alkyl butanoate compounds containing a 2-methyl, 3-thiol group (e.g., ethyl 3-mercapto-2-methylbutanoate). Compounds of this type provide useful organoleptic properties and are generally hedonically pleasing when perceived by a person's olfactory and/or gustatory receptor cells. Several derivatives of these esters, and their thioacetate analogues, are also novel materials that have been found to have with interesting olfactive and/or taste profiles. Accordingly, unique fragrance and flavor compositions containing these compounds are provided.

One aspect of the present invention provides a compound represented by formula (I),

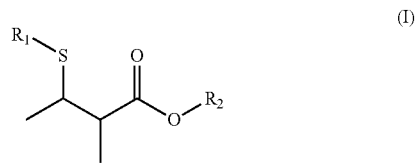

wherein, $R_1$ is hydrogen or an acetyl group and $R_2$ is a $C_{1-3}$ straight chain or branched alkyl group. In one embodiment, the compound wherein $R_1$ is acetyl and $R_2$ is a methyl is excluded from the compounds represented by formula (I).

Another aspect of the present invention provides flavor or fragrance compositions that include at least one compound of formula (I) (including the compound of formula (I) wherein $R_1$ is acetyl and $R_2$ is a methyl). The flavor or fragrance composition may be added to a commercial product to increase and/or improve the taste and/or fragrance of the commercial end product when consumed by a human.

In one embodiment the compound is selected from the group consisting of ethyl 3-mercapto-2-methylbutanoate, methyl 3-mercapto-2-methylbutanoate, methyl 3-acetylthio-2-methylbutanoate and ethyl 3-acetylthio-2-methylbutanoate. In one embodiment, the compound is selected from the group consisting of ethyl 3-mercapto-2-methylbutanoate, methyl 3-mercapto-2-methylbutanoate and ethyl 3-acetylthio-2-methylbutanoate. In one embodiment, the compound is ethyl 3-mercapto-2-methylbutanoate.

DETAILED DESCRIPTION

Definitions

As used herein, the term "fragrance composition" refers to a mixture comprising one or more fragrance components, in any of their forms, and one or more solvents or perfuming co-ingredients. As known in the art, a fragrance composition will contain one or more fragrance components (e.g., perfuming co-ingredients) in order to impart an olfactory note to the composition (e.g., a household cleaner, perfume, or other commercial product) to which it is added. In one embodiment, the fragrance composition contains two or more fragrance components which, collectively and in combination with the solvent to which they are added, impart an intended olfactory note (e.g., a hedonically pleasing "tropical" note) to a human in close proximity to the fragrance composition.

In general terms, perfuming co-ingredients belong to chemical classes as varied as alcohols, aldehydes, ketones, esters, ethers, acetates, nitriles, terpene hydrocarbons, nitrogenous or sulphurous heterocyclic compounds and essential oils of natural or synthetic origin, and are known to perfumists of ordinary skill in the art. Many of these ingredients are listed in reference texts such as S. Arctander, *Perfume and Flavor Chemicals,* 1969, Montclair, N.J., USA or any of its more recent versions, each of which are hereby incorporated by reference.

As used herein, the term "flavor composition" refers to a composition that contains one or more compound(s) (e.g., co-ingredients) that provide(s) a desired taste when combined with a solvent that is suitable for oral administration and oral consumption. Examples of flavoring co-ingredients that are generally included in a flavor composition are listed in S. Arctander, *Perfume and Flavor Chemicals,* 1969, Montclair, N.J., USA. The skilled person in the art of flavors is able to select them on the basis of its general knowledge and according to the nature of the product to be flavored and the desired taste.

As used herein, the phrase "consumer product" or "end product" refers to composition that is in a form ready for use by the consumer for the marketed indication. A solvent suitable for use in a consumer product is a solvent that, when combined with other components of the end product, will not render the consumer product unfit for its intended consumer use.

Any one of the above-described compounds can be included in a fragrance or flavor composition. In one embodiment, any one of the above described compounds is provided in a fragrance composition. In an alternative embodiment, any one of the above-described compounds is provided in a flavor composition.

The compounds of the present invention can be prepared synthetically. In one embodiment, the compounds of the present invention are prepared by a Michael-type addition of thiolacetic acid to an $\alpha,\beta$-unsaturated ester, followed by hydrolysis of the thioacetate to the free thiol. In one embodiment of the present invention, 1 mole of an $\alpha,\beta$-unsaturated ester is refluxed with 1 mole of thiolacetic acid over 3 days to produce the thioacetate intermediate. The thioacetate intermediate is then refluxed with an excess amount of 5% HCl, in an appropriate alcohol, for hydrolysis of the thioacetate to the free thiol. The $\alpha,\beta$-unsaturated esters utilized as starting materials in the present invention, namely ethyl 2-methyl-2-butenoate (ethyl tiglate), methyl 2-methyl-2-butenoate (methyl tiglate) and isopropyl 2-methyl-2-butenoate (isopropyl tiglate) are commercially available to persons of ordinary skill in the art in the flavor and fragrance industry. Food grade tiglate starting materials can be obtained from, for example, Sigma Aldrich (SAFC), St. Louis, Mo.

The synthetic method used in the present invention is preferable to the method described in U.S. Pat. No. 6,878,366, as it reduces, if not avoids, the amount of disulfide products.

Another advantage of the process of the present invention is the production of a thioacetate intermediate represented by compounds of formula (I), in which $R_1$ is acetyl and $R_2$ is a $C_1$-$C_3$ straight chained or branched alkyl group. Compounds of this type can themselves impart hedonically pleasing fragrances and tastes to consumer products.

One or more of the compounds of the present application, alone or in combination with other co-ingredients, can be employed in fragrance and flavor compositions, solvents, media and the like. The use of such compounds is applicable to a wide variety of products in the fragrance industry such as, but not limited to: candles; air fresheners; perfumes; colognes; personal care products such as soaps, deodorants, shampoos, conditioners, shower gels and shaving lotions; cosmetics such as lotions and ointments; as well as detergents; fabric care products and household cleaner/cleaning agents. The use of such compounds is also applicable to a wide variety of products in the flavor industry such as, but not limited to: foodstuffs such as baked goods, dairy products, desserts, etc.; beverages such as juices, sodas, teas, flavored waters, fruit-based "smoothy" drinks, milk-based drinks, etc.; confectionaries such as sweets, hard candy, gums; and gelatinous materials, snacks, desserts, pharmaceuticals, oral care products and the like.

As the compounds of the present invention are useful ingredients for the perfuming or flavoring of various products, the present invention also concerns all different forms of the compounds of the present invention that can be advantageously employed in perfumery or in flavors. Such forms include a composition of matter including, or consisting of (e.g., consisting essentially of) a compound of formula (I) and a solvent commonly used in perfumery or in flavor compositions. Examples of such solvents used in perfumery are known in the art and include, but are not limited to: dipropyleneglycol, diethyl phthalate, isopropyl myristate, benzyl benzoate, 2-(2-ethoxy)-1-ethanol, ethyl citrate, ethanol, water/ethanol mixtures, limonene or other terpenes, isoparaffins such as those known under the trademark Isopar® (ExxonMobil Chemicals, Houston, Tex.), and glycol ethers and glycol ether esters such as those known under the trademark Dowanol® (Dow Chemical Company, Midland Mich.). Examples of solvents commonly used in flavors are also known in the art and include, but are not limited to: propylene glycol, triacetin, triethyl citrate, benzyl alcohol, benzyl benzoate, ethanol, vegetable oils and terpenes.

The compounds of the present invention are particularly valuable as being capable of imparting fruity, juicy, tropical, sweet notes to a fragrance composition. For example, ethyl 3-mercapto-2-methylbutanoate can be used to impart a guava/mango characteristic to fragrance compositions. For fragrance applications, typical concentrations of the compounds of formula (I) are on the order of 0.01 ppm to 1% by weight, or more, based on the total weight of the composition into which the fragrance compound is incorporated. Those skilled in the art will be able to employ the desired level of the compounds of the invention to provide the desired fragrance/flavor and intensity. In general, compounds of the present invention will be used in relatively small amounts, typically via significant dilutions due to their high-impact, diffusive properties.

The perfuming compositions according to the invention may be in the form of a simple mixture of the various co-ingredients and solvents, or also in the form of a biphasic system such as an emulsion or microemulsion. Such systems are well-known to persons skilled in the art.

As mentioned above, suitable perfumed end products that can include a compound of the present invention include, but are not limited to: 1) candles, air fresheners, perfumes and colognes, 2) personal care products such as soaps, deodorants, shampoos, conditioners, shower gels and shaving lotions; 3) cosmetics such as lotions and ointments; as well as 4) detergents, fabric care products and household cleansers/cleaning agents. Depending on the solvents that may be present in some end products, it may be necessary to protect the compounds from premature degradation, for example by encapsulation or with a stabilizer, or other methods well-known to those of ordinary skill in the art.

The compounds of the present invention can also be added to, for example: 1) fragrance products; perfume; eau de perfume; eau de toilet; eau de cologne; and the like; skin-care cosmetics, face washing creams, varnishing creams, cleansing creams, cold creams, massage creams and oils, milky lotions, skin toning lotion, cosmetic solutions, packs, makeup remover, and the like; 2) makeup cosmetics, foundations, face powders, pressed powders, talcum powders, lip sticks, lip creams, cheek powders, eyeliners, mascara, eye shadows, eyebrow pencils, eye packs, nail enamels, nail enamel removers, and the like; 3) hair care cosmetics, pomades, brilliantines, setting lotions, hair sticks, hair solids, hair oils, hair treatments, hair creams, hair tonics, hair liquids, hair sprays, hair restorers, hair dyes, and the like; 4) sunburn cosmetics, suntan products, sunscreen products, and the like; 5) medical cosmetics, antiperspirants, after-shave lotions and gels, permanent wave lotions, medicated soaps, medicated shampoos, medicated skin care products, and the like; 6) hair care products, shampoos, rinses, shampoo-including-rinses, hair conditioners, hair treatments, hair packs, and the like; 7) as soaps, toilet soaps, bath soaps, perfumed soaps, transparent soaps, synthetic soaps, and the like; 8) body washing soaps, body soaps, body shampoos, hand soaps, and the like; 9) bathing, bathing agents (e.g., bath salts, bath tablets, bath liquids, and the like), foam baths (bubble bath and the like), bath oils (e.g., bath perfumes, bath capsules and the like), milk baths, bath gels, bath cubes, and the like; 10) detergents, heavy duty detergents for clothes, light duty detergents for clothes, liquid detergents, laundering soaps, compact detergents, powder soaps, and the like; 11) softening finishing agents, softeners, furniture care products, and the like; and deodorants, aromatic substances and the like; 12) insect repellent, insecticides, and the like; 13) oral care products such as tooth pastes, mouth cleaners, mouth wash, troches, chewing gums, and the like; and 14) pharmaceutical products, poultices, external skin care pharmaceuticals such as ointments, internal administration medicines, and the like.

Furthermore, the compounds of the invention, in any of their forms, can also be incorporated into flavoring compositions or flavored products, together with co-ingredients or adjuvants, e.g., to impart taste to flavoring compositions, foods or beverages. Consequently, the use of the compounds of the present invention, in any of their forms, as flavoring ingredients, is another object of the present invention, as is a flavor composition comprising a compound of the present invention.

In one embodiment, the compound for incorporation into a flavor composition is selected from methyl 3-mercapto-2-methylbutanoate, methyl 3-acetylthio-2-methylbutanoate and ethyl 3-acetylthio-2-methylbutanoate. In one embodiment, the compound for incorporation into a flavor composition is selected from the group consisting of methyl 3-mercapto-2-methylbutanoate and ethyl 3-acetylthio-2-methylbutanoate. In one embodiment, the compounds for incorporation into a flavor composition excludes ethyl 3-mercapto-2-methylbutanoate.

The flavor compositions according to the invention may be in the form of a simple mixture of flavoring ingredients or in an encapsulated form, e.g., a flavoring composition entrapped into a solid matrix that may comprise wall-forming and plasticizing materials such as mono-, di- or trisaccharides, natural or modified starches, hydrocolloids, cellulose derivatives, polyvinyl acetates, polyvinylalcohols, proteins or pectins. Examples of particularly useful matrix materials include, for example, sucrose, glucose, lactose, levulose, fructose, maltose, ribose, dextrose, isomalt, sorbitol, mannitol, xylitol, lactitol, maltitol, pentatol, arabinose, pentose, xylose, galactose, maltodextrin, dextrin, chemically modified starch, hydrogenated starch hydrolysate, succinylated or hydrolysed starch, agar, carrageenan, gum arabic, gum accacia, tragacanth, alginates, methyl cellulose, carboxymethyl cellulose, hydroxyethyl cellulose, hydroxypropylinethyl cellulose, derivatives, gelatin, agar, alginate and mixtures thereof. Encapsulation is well-known to persons skilled in the art, and may be performed, for instance, using techniques such as spray-drying, agglomeration or extrusion, or coating encapsulation, including coacervation and complex coacervation techniques.

The compounds of the present invention are particularly valuable as being capable of imparting tropical, berry and vegetable notes, as well as creaminess to flavor ingredients. Specifically, ethyl 3-mercapto-2-methylbutanoate can be used to impart a guava characteristic to flavor compositions. For flavor applications, typical concentrations of compounds of formula (I) are on the order of 0.1 ppb-100 ppm. Preferably, applicable concentrations fall in the range of 0.001 ppm-0.01 ppm. The compounds of the present invention have been found to enhance the flavor of pineapple, guava, grapefruit and other tropical fruits at a concentration of about 0.005 ppm. Those skilled in the art will be able to employ the desired level of said compounds to provide the desired flavor and intensity. Much higher concentrations may be employed when the compounds are used in concentrated flavors and flavor compositions.

In one embodiment, a compound of the present invention is included/used in chewing and bubble gums and confectionaries (e.g., hard or soft candies or lozenges). Chewing gum compositions typically include one or more gum bases and other standard components such as flavoring agents, softeners, sweeteners and the like. Flavoring agents for use in chewing gum compositions are well known and include natural flavors such as citrus oils, peppermint oil, spearmint oil, oil of wintergreen, natural menthol, cinnamon, ginger and the like; artificial flavors such as menthol, carvone, limonene, cinnamic aldehyde, linalool, geraniol, ethyl butyrate, and the like. As is known in the art, the ingredients used in chewing gum compositions can include sweeteners, both natural and artificial and both sugar and sugarless. Sweeteners are typically present in the chewing gum compositions in amounts of from about 20% to 80% by weight, preferably from about 30% to 60% by weight, based on the total weight of the chewing gum composition. Sugarless sweeteners include, but are not limited sugar alcohols such as Sorbitol, manifold, xylitol, hydrogenated starch hydrolysates, malitol and the like. High intensity sweeteners such as sucralose, aspartame, neotame, salts of acesulfame, and the like, when employed, are typically present up to about 1.0% by weight.

In an alternative embodiment, a compound of the present invention is included in an oral personal care product (e.g., a mouthwash or toothpaste). For example, a mouthwash can be prepared by dissolving a flavor composition (e.g., a flavor cocktail) (liquid or powder) that includes a compound of the present invention in a solvent (e.g., water) that further includes, for example, a flavor such as menthol and a surfactant; and then mixing the resulting solution with, for example, an aqueous erythritol solution.

In one embodiment of the present invention, a compound of the present invention is added, directly or indirectly, to a pharmaceutical dosage form (e.g., a tablet, capsule, drop or lozenge) that contains a therapeutically active agent (e.g., a medicament). For example, one embodiment of the present invention provides a cough drop or lozenge containing one or more compounds of the present invention and, optionally, further containing menthol or other medicaments for the treatment of sore throat, coughing or other upper respiratory ailments.

One or more of the present compounds can also be added to, for example, compositions for the preparation of: 1) carbonated or non-carbonated fruit beverages, carbonated cola drinks, wine coolers, fruit liquors, cordials, milk drinks, smoothy drinks, flavored water, tropical alcoholic and "virgin" drink mixes (e.g. margarita, piña colada or "rum-runner" concentrates), and powders for drinks (e.g., powdered sports or "hydrating" drinks); 2) frozen confectioneries such as ice creams, sherbets, and ice-lollies, hard candies, soft candies, taffies, chocolates, and sugarless candies; 3) desserts such as jelly and pudding; 4) confectioneries such as cakes, cookies, chewing gums and bubble gums; 5) condiments, spices and seasonings, dry cereals, oatmeals, and granola bars; 6) alcoholic beverages, energy beverages, juices, teas, coffees, salsa, and gel beads; 7) film strips for halitosis, and oral personal care products; 8) gelatin candies, pectin candies, starch candies, lozenges, cough drops, throat lozenges, throat sprays, and toothpastes.

The present compounds may also be added to, for example; 1) Japanese confectioneries such as buns with bean-jam filling, bars of sweet jellied bean paste, and sweet jellied pounded rice; 2) jams; candies; 3) breads; 4) beverages such as green tea, oolong tea, black tea, persimmon leaf tea, Chamomile tea, Sasa veitchii tea, mulberry leaf tea, Houttuynia cordata tea, Puer tea, Mate tea, Rooibos tea, Gimunema tea, Guava tea, coffee, espresso, and hot and cold espresso and coffee products obtained by mixing espresso and/or coffee with milk, water or other liquids suitable for oral consumption (e.g., lattes, cafe au lait, cafe mocha) and cocoa; 5) soups such as Japanese flavor soup, western flavor soup, and Chinese flavor soup; 6) seasonings; 7) various instant beverages and foods; 8) various snack foods; and 9) other compositions for oral use.

EXAMPLES

The present application is further described by means of the examples, presented below, wherein the abbreviations have the usual meaning in the art. The temperatures are indicated in degrees centigrade (° C.); the NMR spectral data were recorded in $CDCl_3$ with a 500 MHz machine for $^1H$ and $^{13}C$, the chemical displacements are indicated in ppm with respect to TMS as the standard, and the J-coupling constants are expressed in Hz.

The use of such examples is illustrative only and in no way limits the scope and meaning of the invention or of any exemplified term. Likewise, the invention is not limited to any particular preferred embodiments described herein. Indeed, many modifications and variations of the invention will be apparent to those skilled in the art upon reading this specification. The invention is therefore to be limited only by the terms of the appended claims along with the full scope of equivalents to which the claims are entitled.

Example 1

Synthesis of Ethyl 3-acetylthio-2-methylbutanoate

Ethyl tiglate (10 g) (Bedoukian Research Inc., Danbury, Conn.) and thiolacetic acid (5.9 g) were refluxed at 150° C. over 3 days. Unconverted starting materials were distilled (7 T, 35° C.). The undistilled thick red oil was subjected to column chromatography (2% ethyl acetate in hexanes), and after concentration of solvent yielded a clear oil (6.4 g, 40%) as a mixture of stereoisomers. Odor: at 1000 ppm in DPG— cooked onions, tropical fruit. GC/MS (EI): m/z (%) 204(4), 161(78), 129(19), 115(30), 102(24), 56(32), 43(100). $^1H$ NMR ($CDCl_3$); δ 4.08-4.17 (m, 2H), 3.84-3.93 (m, 1H), 2.59-2.76 (m, 1H), 2.30 (s, 3H), 1.17-1.33 (m, 9H)). $^{13}C$ NMR ($CDCl_3$): δ 194.9, 174.0, 60.6, 44.8, 30.7, 19.4, 18.5, 14.6, 14.2.

Example 2

Synthesis of Ethyl 3-mercapto-2-methylbutanoate

The crude product of Example 1 prior to column chromatography (~9 g) was refluxed with 10 mL ethanol and several drops of 10M HCl (in ethanol) for 12 hours. Distillation (8.5 T, 75° C.) afforded the free thiol as a clear oil (3.7 g, 52%) and as a mixture of stereoisomers. Odor: at 1 ppm in DPG— guava, mango, exotic fruity note, juicy, sweet, tropical and ripe. GC/MS (EI): m/z (%) 162(34), 134(2), 129(34), 89(52), 74(77), 56(100). $^1H$ NMR ($CDCl_3$); δ 4.08-4.17 (m, 2H), 3.14-3.31 (m, 1H), 2.46-2.58 (m, 1H), 1.67 & 1.50 (2d, J=7.79 Hz, 1H mix of diastereomers), 1.17-1.35 (m, 9H)). $^{13}C$ NMR ($CDCl_3$) for mix of diastereomers: δ 174.6, 60.9, 60.6, 48.8, 47.7, 37.8, 23.6, 21.9, 14.3, 13.5.

Example 3

Synthesis of Methyl 3-acetylthio-2-methylbutanoate

Conditions are the same as for Example 1, but with methyl tiglate (Sigma Aldrich, St. Louis, Mo.) as the starting component; 35% yield. Odor: at 100 ppm in DPG—fruity, sulfur, green, fatty, onion. GC/MS (EI): m/z (%) 190(4), 160 (1), 147(60), 115(31), 88(36), 83(12), 73(2), 59(36), 56(21), 43(100). $^1H$ NMR ($CDCl_3$): δ 3.83-3.93 (m, 1H), 3.67 (2s mix of isomers, 3H), 2.62-2.78 (m, 1H), 2.29 (s, 3H), 1.26-1.32 (2d mix of isomers, J=6.83 Hz, 3H), 1.16-1.20 (2d mix of isomers, J=7.33 Hz, 3H)). $^{13}C$ NMR ($CDCl_3$): δ 194.9, 174.5, 52.0, 44.7, 41.7, 30.7, 19.3, 14.6.

Example 4

Synthesis of Methyl 3-mercapto-2-methylbutanoate

Conditions are the same as for Example 2, but with the product of Example 3 as the starting component and methanol as solvent; 44% yield. Odor: at 0.1 ppm in DPG—onions, green vegetable, peach, tropical fruit, metallic. GC/MS (EI): m/z (%) 148(46), 115(25), 88(100), 61(64), 59(100). $^1H$ NMR ($CDCl_3$): δ 3.69 (s mix of isomers, 3H), 3.13-3.30 (m, 1H), 2.48-2.58 (m, 1H), 1.66 & 1.51 (2d, J=7.34 Hz, 1H mix of diastereomers), 1.31-1.34 (2d mix of isomers, J=6.87 Hz, 3H), 1.18-1.27 (2d mix of isomers, J=6.87 Hz, 3H). $^{13}C$ NMR ($CDCl_3$) for mix of diastereomers: δ 175.0, 51.9, 51.6, 48.7, 47.6, 37.7, 37.1, 23.5, 21.9, 14.3, 13.5.

Example 5

Synthesis of Isopropyl 3-acetylthio-2-methylbutanoate

Conditions are the same as for Example 1, but with isopropyl tiglate (Sigma Aldrich, St. Louis, Mo.) as the starting component; 65% yield. Odor: at 100 ppm in DPG—overripe fruit, green, fatty, orange, sparkling. GC/MS (EI): m/z (%) 218(5), 175(98), 133(32), 83(31), 56(49), 43(100). $^1H$ NMR ($CDCl_3$): δ 4.96-5.04 (m, 1H), 3.84-3.89 (m, 1H), 2.56-2.70 (m, 1H), 2.30 (s, 3H), 1.28-1.33 (2d mix of isomers, J=6.87

Hz, 3H), 1.16-1.25 (m, 9H)). $^{13}$C NMR (CDCl$_3$): δ 195.0, 173.5, 68.0, 44.9, 41.6, 30.7, 21.8, 19.5, 14.6.

Example 6

Synthesis of Isopropyl 3-mercapto-2-methylbutanoate

Conditions are the same as for Example 2, but with the product of Example 5 as the starting component and isopropyl alcohol as solvent; 37% yield. Odor: at 1 ppm in DPG—exotic fruit, sweet, sulfury, fatty, floral, slightly rosy. GC/MS (EI): m/z (%) 176(48), 143(14), 134(72), 117(51), 89(91), 61(93), 56(100). $^1$H NMR (CDCl$_3$): δ 4.98-5.05 (m, 1H), 3.14-3.30 (m, 1H), 2.42-2.53 (m, 1H), 1.67 & 1.49 (2d, J=7.33 Hz, 1H mix of diastereomers), 1.31-1.35 (m, 3H), 1.17-1.25 (m, 9H). $^{13}$C NMR (CDCl$_3$) for mix of diastereomers: δ 174.2, 68.3, 67.6, 48.8, 47.9, 37.8, 23.6, 21.8, 14.2, 13.5.

Example 7

Fragrance Composition

The following fragrance composition having a guava, fruity note was prepared. Amounts are based on 1000 total parts:

| COMPONENT | PARTS PER THOUSAND |
|---|---|
| ACETYL ISO EUGENOL | 1.500 |
| ETHYL 3-MERCAPTO-2-METHYLBUTANOATE 100 PPM IN TEC (TRIETHYL CITRATE) | 30.000 |
| ALLYL CAPROATE | 50.000 |
| ANISYL PROP | 0.500 |
| BENZ ISO VAL | 10.000 |
| BENZALD | 0.100 |
| BUTYL BENZOATE | 1.000 |
| CELERY SEED OIL (REYNAUD) NAT | 2.000 |
| CITRONELLYL PROP, L, (AVAILABLE FROM TAKASAGO IN'TL CORP.) | 0.500 |
| DECALACTONE, DELTA | 2.500 |
| 1,1-DIMETHYL-2-PHENYLETHYL BUTANOATE | 235.000 |
| DIPROPYLENE GLYCOL | 537.300 |
| ETH ACETATE | 1.000 |
| ETH AMYL KETONE | 1.000 |
| ETH BUTY | 20.000 |
| ETH CAPRATE | 1.000 |
| ETH CAPROATE | 0.100 |
| ETH CAPRYLATE | 1.000 |
| ETH ISO VALERATE | 1.000 |
| ETH PROPANOATE | 1.000 |
| HEXENOL, TRANS-2 | 25.000 |
| ISO AMYL ISO BUTY | 1.000 |
| ISO BORNYL ACET | 5.000 |
| LEMON OIL CALIFORNIA | 2.000 |
| METH 2-METH BUTANOATE | 1.000 |
| PEPPERMINT OIL WILLAMET NAT ? | 2.000 |
| PHEN ETHYL ISO VALERATE | 60.000 |
| SPEARMINT OIL NATIVE REDIST NAT | 0.500 |
| UNDECALACTONE, DELTA | 2.000 |
| UNDECALACTONE, GAMMA | 2.000 |
| VANILLIN | 3.000 |

Example 8

Flavor Composition

A guava flavor was prepared consisting of the following ingredients, based on 100 total parts

| Ingredient | Parts Per Hundred |
|---|---|
| Ethyl Alcohol | 94.3860 |
| Acetoin | 0.3500 |
| Acetic Acid | 0.8400 |
| Caproic Acid | 0.1100 |
| Limonene | 0.1500 |
| Ocimene | 0.0400 |
| Caryophellene | 0.0200 |
| Cis-3-Hexenol | 0.2600 |
| Hexanol | 3.6000 |
| Nerolidol | 0.1300 |
| Phenylethyl Acetate | 0.0300 |
| Phenyl Acetic Acid | 0.0300 |
| Phenylethyl Alcohol | 0.0300 |
| Cinnamic Acid | 0.0070 |
| Cinnamyl Acetate | 0.0100 |
| Ethyl 3-Mercapto-2-Methylbutanoate (1% (w/w) dissolved in ethanol) | 0.0070 |
| Total | 100 |

Example 9

Chewing Gum Composition

A flavored chewing gum may be prepared from the ingredients shown below:

| Ingredient | Parts Per Hundred |
|---|---|
| Chewing gum Base | 97.00 |
| Citric acid | 1.00 |
| Flavor containing .01 ppm of ethyl 3-mercapto-2-methylbutanoate | up to 2.0 |
| Total | 100.00 |

Example 10

Chewy Candy Composition

A chewy candy may be prepared from the ingredients shown below:

| Ingredient | Weights (g) |
|---|---|
| 42 DE Corn Syrup | 500 |
| Sugar | 390 |
| Water | 130 |
| Gelatin | 17.5 |
| Water, Hot (176-194 F.) | 35 |
| Sugar | 17.5 |
| Palm Kernel Oil | 45 |
| Lecithin | 3 |
| Powdered Sugar | 26 |
| Acid | up to 1% |
| Flavor containing .01 ppm of ethyl 3-mercapto-2-methylbutanoate | up to 1.2% |

Example 11

Pressed Candy Composition

A pressed candy may be prepared from the ingredients shown below:

| Ingredient | Parts Per Hundred |
| --- | --- |
| Sorbitol P60W | 95.45 |
| Citric Acid | 0.50 |
| Malic Acid | 0.50 |
| Sucralose | 0.15 |
| Magnesium Stearate | 0.80 |
| Flavor containing .01 ppm of ethyl 3-mercapto-2-methylbutanoate | up to 2.6 |
| Total | 100.00 |

Example 12

Hard Candy Composition

A hard candy may be prepared from the ingredients shown below:

| Ingredient | Parts Per Hundred |
| --- | --- |
| sucrose | 79.0 |
| Corn syrup, 42 DE | 19.0 |
| HFCS 55 | 1.0 |
| Flavor containing .01 ppm of ethyl 3-mercapto-2-methylbutanoate | up to .6 |
| Citric acid | 0.2 |
| Malic acid | 0.2 |
| Total | |

Example 13

A Chewing Gum Composition

A flavored chewing gum having a strawberry lime flavor may be prepared from the ingredients shown below:

| Ingredient | Parts Per Hundred |
| --- | --- |
| Chewing gum Base | 97.10 |
| Citric acid | 1.00 |
| Art Strawberry Fl OS | 1.00 |
| Vivid ™ N&A Fl Key Lime type OS | 0.60 |
| Flavor containing .01 ppm of ethyl 3-mercapto-2-methylbutanoate | 0.30 |
| Total | 100.00 |

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all values are approximate, and are provided for description.

Patents, patent applications, publications, product descriptions, and protocols are cited throughout this application, the disclosures of each of which is incorporated herein by reference in its entirety for all purposes.

The invention claimed is:

1. A guava fragrance composition for addition to a consumer product comprising ethyl 3-mercapto-2-methylbutanoate in an amount effective to impart a guava fragrance to the consumer product.

2. The composition of claim 1, further comprising a solvent suitable for use in a consumer product.

3. The composition of claim 2, wherein the solvent is suitable for topical administration to the skin of a human.

4. The composition of claim 2, wherein the solvent is selected from the group consisting of dipropyleneglycol, diethyl phthalate, isopropyl myristate, benzyl benzoate, 2-(2-ethoxyethoxy)-1-ethanol, ethyl citrate, ethanol, water/ethanol mixtures, limonene, a terpene, an isoparaffin, a glycol ether, a glycol ether ester, and a combination thereof.

5. A consumer product containing the composition of claim 1.

6. The consumer product of claim 5, selected from the group consisting of a candle, an air care product, a perfume, a cologne, a soap, a personal care product, a detergent, a fabric care product and a household cleaning product.

7. The consumer product of claim 5, selected from the group consisting of an air care product, a perfume and a cologne.

8. The consumer product of claim 5, selected from the group consisting of a beverage, a powder or semi-frozen/frozen concentrate for a drink, a candy, a sugarless candy, a chocolate, a chewing gum, a bubble gum, a condiment, a spice, a seasoning, a dry cereal, an oatmeal, a granola bar, an alcoholic beverage, an energy beverage, a juice, a tea, a coffee, a salsa, a gel bead, a film strip for halitosis, a lozenge, a cough drop, a throat lozenge, a throat spray, a toothpaste and a mouth rinse.

9. The consumer product of claim 8, selected from the group consisting of a beverage, a chewing gum and a bubble gum.

10. A method of imparting a fragrance to a consumer product comprising adding to the consumer product the fragrance composition of claim 1 in an amount effective to impart a fragrance to the consumer product.

11. A cologne or perfume that imparts a guava fragrance comprising ethyl 3-mercapto-2-methylbutanoate and a solvent suitable for topical administration to the skin of a human.

12. The composition of claim 1, wherein ethyl 3-mercapto-2-methylbutanoate is present in an amount of from about 0.01 ppm to about 1% weight by weight in the composition.

* * * * *